United States Patent
Kopaciewicz et al.

[11] Patent Number: 5,833,860
[45] Date of Patent: Nov. 10, 1998

[54] CENTRIFUGAL ADSORPTIVE SAMPLE PREPARATION DEVICE AND METHOD

[75] Inventors: William Kopaciewicz, West Newbury; Ingeborg Cann, Hathorne; Donald G. Sheer, Norfolk, all of Mass.

[73] Assignee: Millipore Investment Holdings Limited, Wilmington, Del.

[21] Appl. No.: 623,688

[22] Filed: Mar. 29, 1996

Related U.S. Application Data

[60] Provisional application No. 60/002,879, Aug. 28, 1995.

[51] Int. Cl.⁶ .................................................. B01D 61/00
[52] U.S. Cl. .................... 210/650; 210/767; 210/321.75; 210/502.1; 210/490; 210/500.36; 210/473; 210/477; 210/360.1; 210/380.1; 156/9
[58] Field of Search ........................... 210/502.1, 500.27, 210/490, 500.36, 473, 477, 650, 767, 656, 360.1, 380.1, 651, 321.75; 156/9; 494/36

[56] References Cited

U.S. PATENT DOCUMENTS

| | | | |
|---|---|---|---|
| 3,407,096 | 10/1968 | Landi | 136/86 |
| 3,407,249 | 10/1968 | Landi | 264/49 |
| 3,591,010 | 7/1971 | Pall | 210/505 |

(List continued on next page.)

FOREIGN PATENT DOCUMENTS

| | | |
|---|---|---|
| 0 127 737 | 12/1984 | European Pat. Off. . |
| 0 158 463 | 10/1985 | European Pat. Off. . |
| 0 248 524 | 12/1987 | European Pat. Off. . |
| 0 505 118 | 9/1992 | European Pat. Off. . |
| 0 569 115 | 11/1993 | European Pat. Off. . |
| 0 588 564 | 3/1994 | European Pat. Off. . |
| 2 330 694 | 11/1975 | France . |
| 0 594 506 | 4/1994 | France . |
| 1197587 | 7/1970 | United Kingdom . |
| 1247992 | 9/1971 | United Kingdom . |
| 1548026 | 7/1979 | United Kingdom . |
| 85/01941 | 5/1985 | WIPO . |
| 91/07648 | 5/1991 | WIPO . |
| 95/27546 | 10/1995 | WIPO . |
| 95/27561 | 10/1995 | WIPO . |

OTHER PUBLICATIONS

3M Empore; The revolutionary particle–loaded membrane. Reliable. Efficient. Proven. brochure (8–pages).
QIAGEN Product Guide 1995; "QIAGEN Technologies and Products"; pp. 3–7.
QIAGEN Product Guide 1996; "QIAprep plasmid Miniprep Kits"; pp. 25–27.
Marcel Dekker, Inc.; "Immunodiagnosis of Cancer Second Edition"; Herberman and Mercer; pp. 555–586.
MILLIPORE "What this centrifugal filter pulls out of a small volume sample . . . "; 2–Pages.

(List continued on next page.)

Primary Examiner—Ana Fortuna
Attorney, Agent, or Firm—Nields, Lemack & Dingman

[57] ABSTRACT

Adsorptive sample preparation device and method effective for concentrating, desalting and/or purifying biomolecules. An adsorptive membrane is used to bind biomolecules, which biomolecules can then be eluted with a suitable desorption agent. In a preferred form, the adsorptive filter means is a particle-laden semipermeable membrane having at least one of its major surfaces, preferably both of its major surfaces, covered with a thin fabric. In the method of the invention for concentrating biomolecules or desalting or purify from a solution, the sample reservoir of the above-described adsorptive sample preparation device is filled with an analyte solution, placed in a fixed angle or swinging bucket centrifuge rotor, the solution is driven through the membrane, and analyte obtained as a result of adsorption on the membrane is recovered by washing and then eluting with a suitable desorption agent. A method of sealing the membrane in the device is also set forth.

27 Claims, 11 Drawing Sheets

U.S. PATENT DOCUMENTS

| | | | |
|---|---|---|---|
| 3,888,629 | 6/1975 | Bagshawe | 23/230 B |
| 4,153,661 | 5/1979 | Ree et al. | 264/120 |
| 4,208,194 | 6/1980 | Nelson | 55/158 |
| 4,350,594 | 9/1982 | Kawai et al. | 210/637 |
| 4,373,519 | 2/1983 | Errede et al. | 128/156 |
| 4,460,642 | 7/1984 | Errede et al. | 428/283 |
| 4,565,663 | 1/1986 | Errede et al. | 264/120 |
| 4,632,761 | 12/1986 | Bowers et al. | 210/650 |
| 4,663,049 | 5/1987 | Kolff et al. | 210/641 |
| 4,699,717 | 10/1987 | Riesner et al. | 210/635 |
| 4,705,753 | 11/1987 | Gregor et al. | 435/180 |
| 4,722,898 | 2/1988 | Errede et al. | 435/182 |
| 4,755,301 | 7/1988 | Bowers et al. | 210/650 |
| 4,774,058 | 9/1988 | Mehl | 422/101 |
| 4,797,259 | 1/1989 | Matkovich et al. | 422/101 |
| 4,810,381 | 3/1989 | Hagen et al. | 210/502.1 |
| 4,871,671 | 10/1989 | Errede et al. | 435/182 |
| 4,906,378 | 3/1990 | Hagen et al. | 210/635 |
| 4,971,697 | 11/1990 | Douden et al. | 210/502.1 |
| 4,971,736 | 11/1990 | Hagen et al. | 264/22 |
| 5,003,047 | 3/1991 | Yarmush et al. | 530/413 |
| 5,019,232 | 5/1991 | Wilson et al. | 204/182.8 |
| 5,071,610 | 12/1991 | Hagen et al. | 264/120 |
| 5,112,490 | 5/1992 | Turpen | 210/645 |
| 5,113,860 | 5/1992 | McQuinn | 128/632 |
| 5,124,041 | 6/1992 | Sheer et al. | 210/641 |
| 5,147,539 | 9/1992 | Hagen et al. | 210/502.1 |
| 5,207,915 | 5/1993 | Hagen et al. | 210/635 |
| 5,209,967 | 5/1993 | Wright et al. | 428/283 |
| 5,234,840 | 8/1993 | Appleton | 436/518 |
| 5,238,621 | 8/1993 | Hagen et al. | 264/45.3 |
| 5,248,428 | 9/1993 | Hagen et al. | 210/656 |
| 5,259,951 | 11/1993 | Arright et al. | 210/660 |
| 5,264,184 | 11/1993 | Aysta et al. | 422/101 |
| 5,275,880 | 1/1994 | Boyer, III et al. | 428/328 |
| 5,278,377 | 1/1994 | Tsai | 219/759 |
| 5,279,742 | 1/1994 | Markell et al. | 210/638 |
| 5,288,415 | 2/1994 | Chen-Wu et al. | 210/781 |
| 5,328,756 | 7/1994 | Wright et al. | 428/220 |
| 5,328,758 | 7/1994 | Markell et al. | 428/281 |
| 5,340,746 | 8/1994 | Hagen et al. | 436/109 |
| 5,354,603 | 10/1994 | Errede et al. | 428/240 |
| 5,366,632 | 11/1994 | Balsimo et al. | 210/777 |
| 5,383,573 | 1/1995 | Balsimo | 221/264 |
| 5,391,298 | 2/1995 | Pieper et al. | 210/638 |

OTHER PUBLICATIONS

Cancer Research 49, 1361–1365, Mar. 15, 1989; "Incidence of Serum Antibody Reactivity to Autologous Head and Neck Cancer Cell Lines and Augmentation of Antibody Reactivity following Acid Dissociation and Ultrafiltration"; Vlock, et al.

Cancer Immunol Immunother (1992) 34; 329–336; "Serial studies of autologous antibody reactivity to squamous cell carcinoma of the head and neck"; Vlock, et al.

Biochimica et Biophysica Acta. 1080 (1991) 1–10; Purification and partial characterization of a shed 66 kDa melanoma=associated antigen identified by autologous antibody; Vlock, et al.

The American Society for Clinical Investigation, Inc. vol. 81, Jun. 1988, 1746–1751; "Isolation and Partial Characterization of Melanoma–associated Antigens Identified by Autologous Antibody"; Vlock et al.

The Journal of Urology vol. 150, 100–105, Jul. 1993; "Serum prostate specific antigen complexed to 1–antichymotrypsin as an indicator of prostate cancer"; Christensson, et al.

Journal of Clinical Oncology, vol. 11, No. 12 (Dec.), 1993; pp. 001–007; "Clinical Correlates of circulating immune complexes and antibody reactivity in squamous cell carcinoma of the head and neck"; Vlock et al.

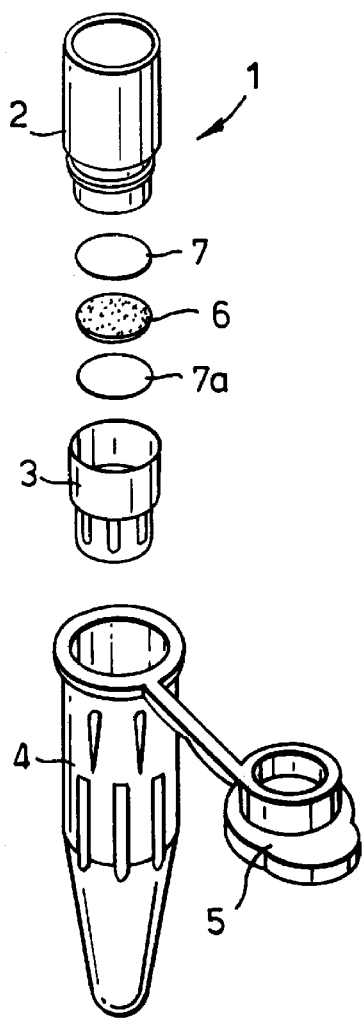
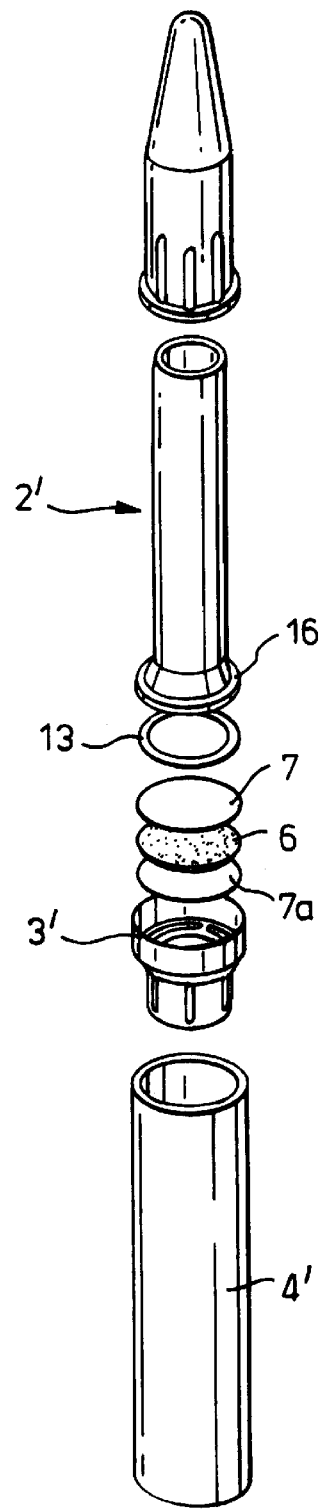
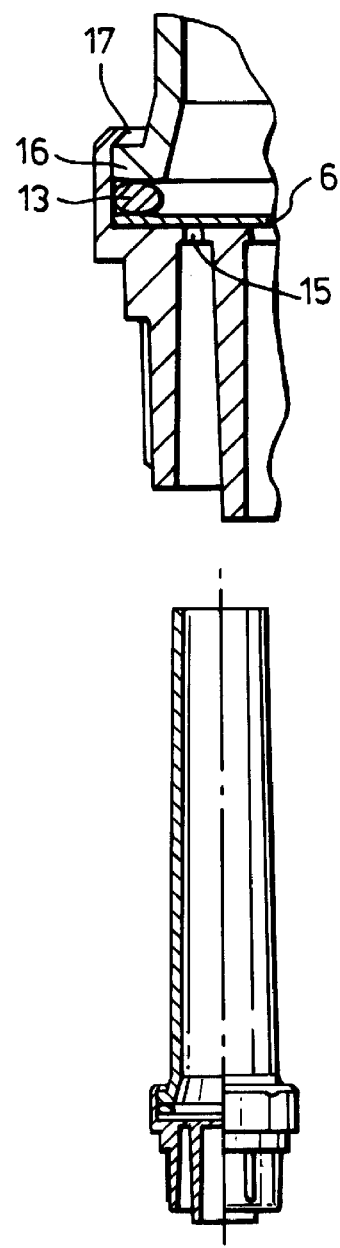

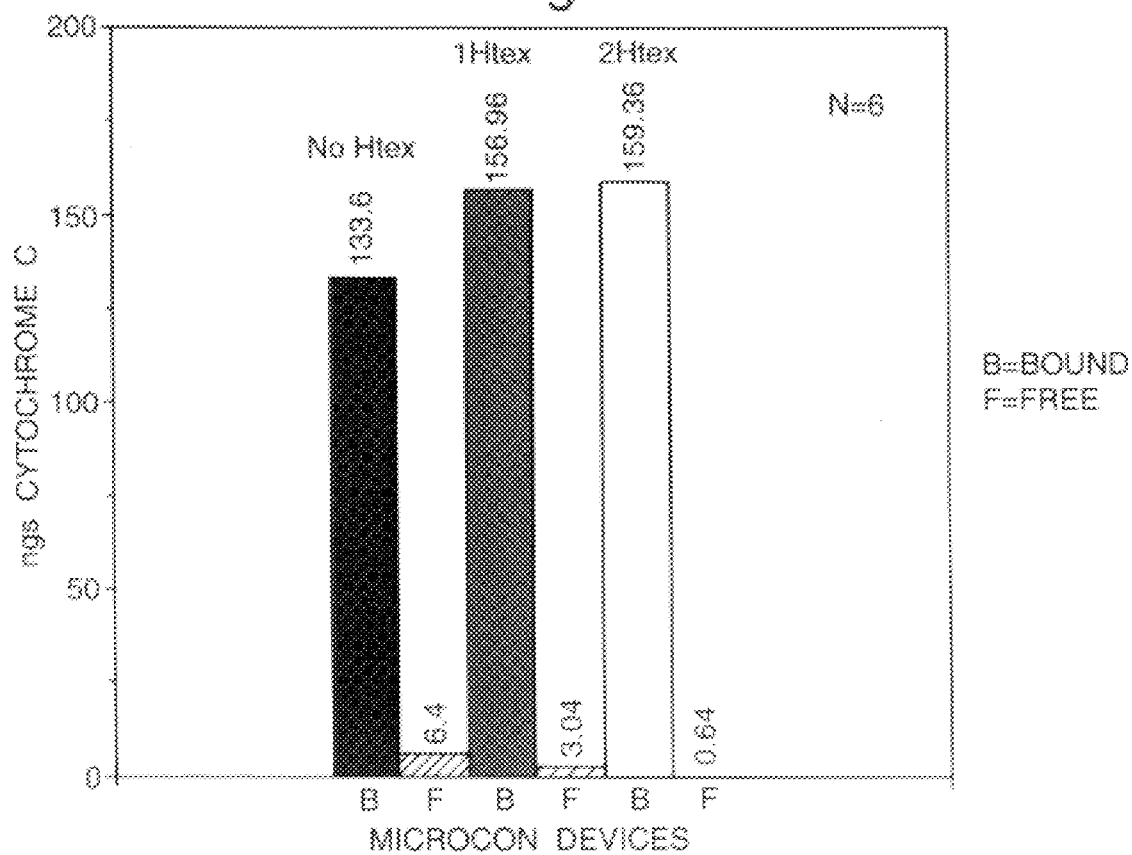

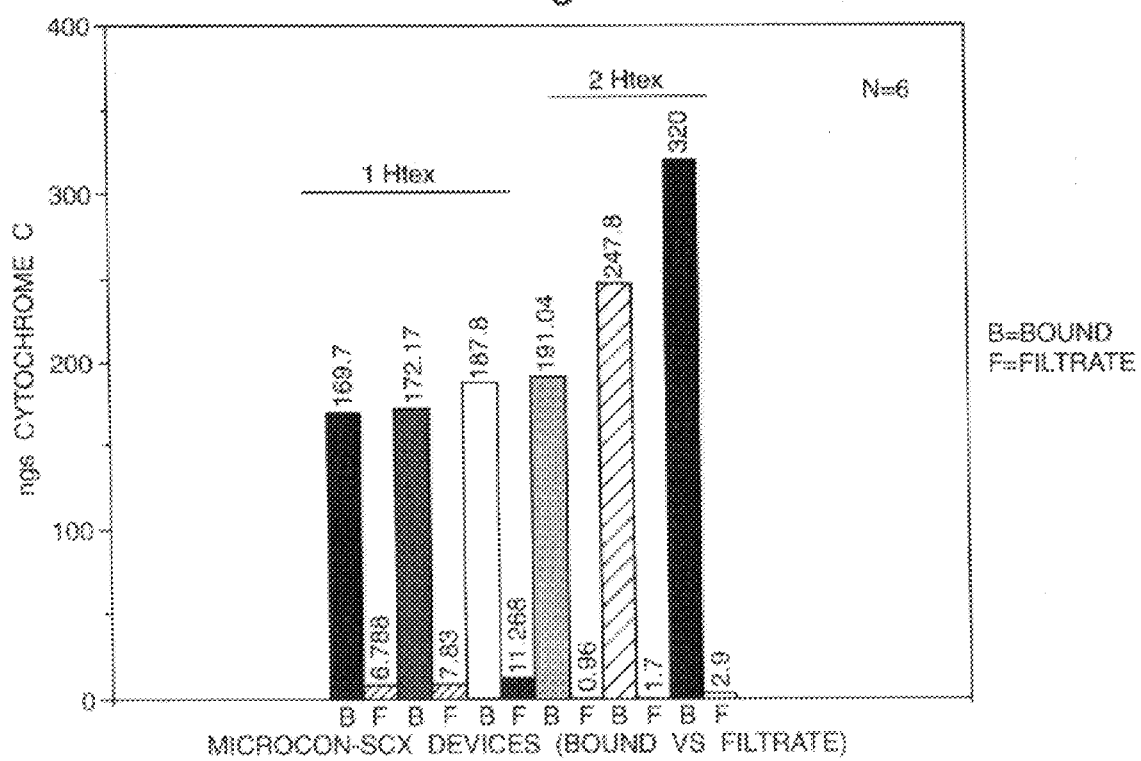

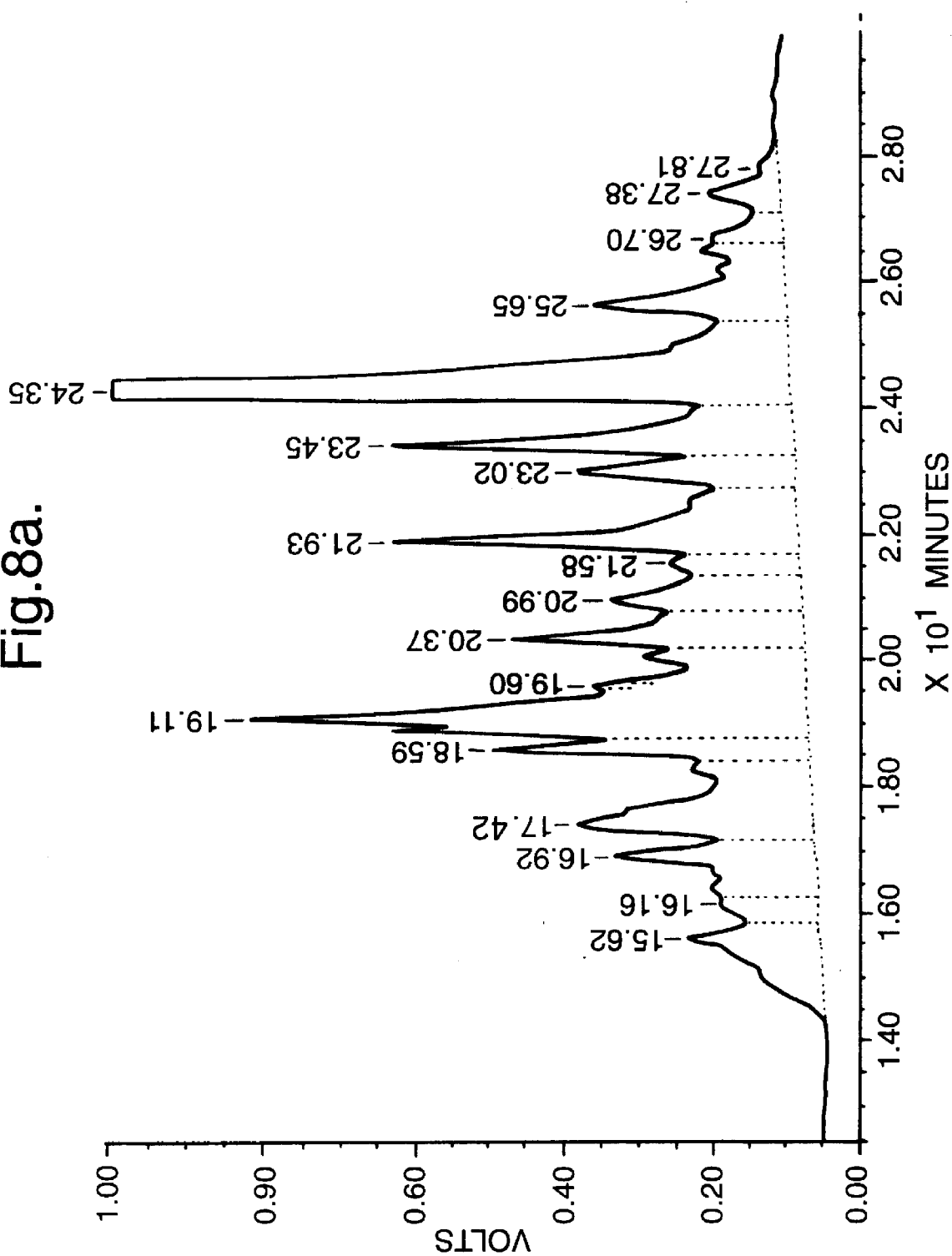

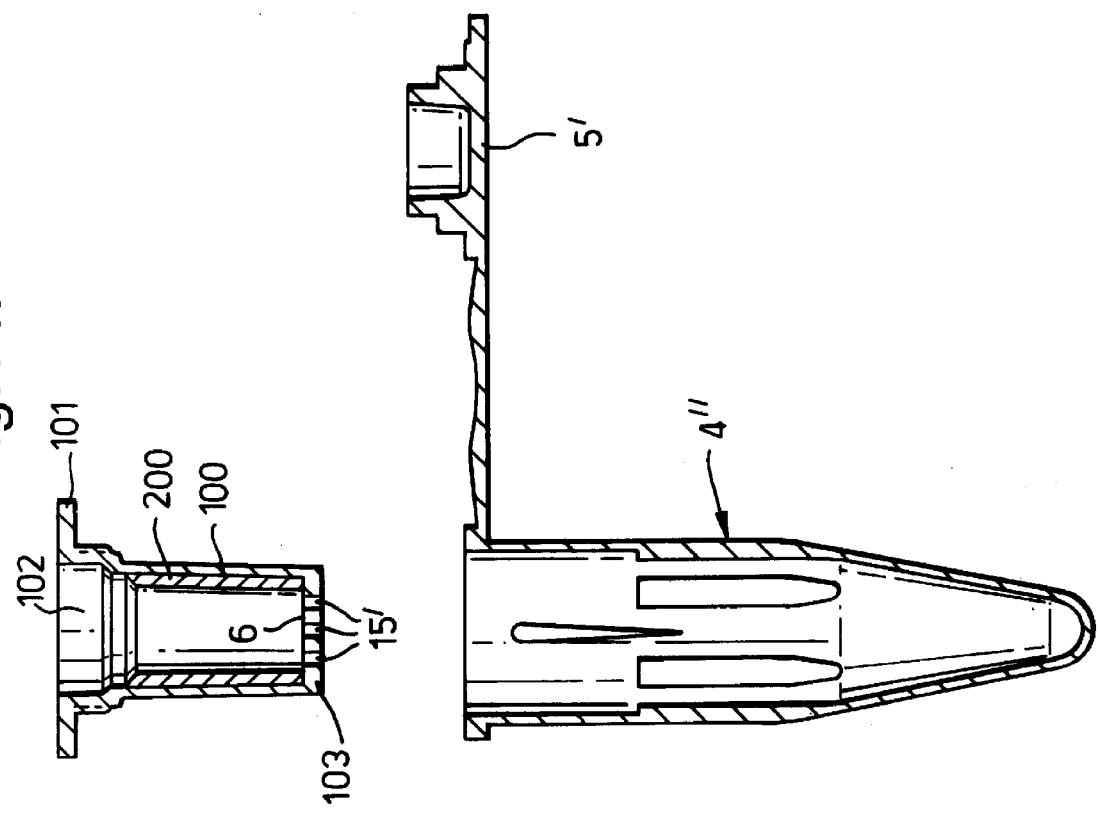
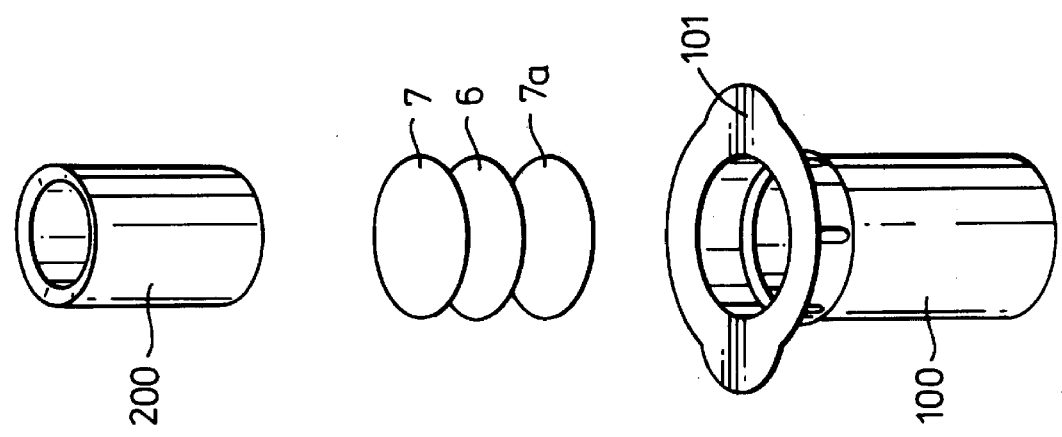

CENTRIFUGAL ADSORPTIVE SAMPLE PREPARATION DEVICE AND METHOD

BACKGROUND OF THE INVENTION

This application claims the benefit of U.S. Provisional Application No. 60/002,879, filed Aug. 28, 1995.

This invention relates to centrifugal methods and devices for concentrating biomolecules from solutions and for recovering a maximal amount of concentrated retentate; adsorptive membranes effective for concentrating biomolecules from solutions; and a method of sealing such membranes in such devices.

A number of analytical procedures have been developed in the biochemical art wherein it is required to remove solvent from peptide solutions in order to have a more concentrated peptide sample which can be analyzed effectively, or to remove or exchange low molecular weight ions or other solutes. Many other analytical procedures, involving not only peptides but biomolecular species in general (e.g., oligonucleotides), also have been developed wherein it is necessary to concentrate and/or "desalt" a biomolecular component in a liquid sample, as there is commonly a need in biochemistry/medicinal chemistry for pure analytes devoid of salts, detergents and other low molecular contaminants. The presence of these substances can be deleterious, in that they often interfere with subsequent chemical analyses or biochemical assay.

U.S. Pat. No. 4,755,301 discloses a centrifugal method and apparatus for concentrating biomolecules without filtering to dryness. A semipermeable ultrafiltration membrane separates a sample reservoir from a filtrate cup, and filtrate ducts below the membrane are offset sufficiently inward from the edge of the membrane so that when the apparatus is used in a fixed angle centrifuge rotor, filtration stops once the retentate meniscus reaches the centrifugal radial level of the outermost edge of the outermost filtrate duct.

Such ultrafiltration devices are commonly used for the "purification" and/or sample preparation of biomolecules and other macromolecules. For such a process to be successful, a membrane must be selected that retains the molecules of interest, yet passes the smaller impurities. Although this scenario is relatively straightforward for analytes greater than about 10,000 molecular weight, it becomes increasingly problematic for substances less than about 5000 molecular weight. The reason is due to the fact that the required membrane porosity to retain the about 10,000 molecular weight analyte is so low that the water permeability (flow rate) becomes poor and processing times too long. For example, a typical centrifugal "spin time" for a device using a membrane suitable for analytes having a molecular weight of 30,000 or more is about one hour, whereas as many as six hours may be required for analytes of about 1000 molecular weight. Furthermore, such long term exposure to high g-force frequently induces device failure.

It is therefore an object of the present invention to provide an adsorptive centrifugal sample preparation device which can concentrate and/or desalt biomolecules from a solution.

It is another object of the present invention to provide a centrifugal recovery process for the recovery of a maximal amount of concentrated macromolecular retentate from a centrifugal concentrator device.

It is a further object of the present invention to provide a reusable centrifugal microconcentrator.

It is a still further object of the present invention to provide a centrifugal microvolume concentrator that is economic to manufacture.

It is another object of the present invention to provide sample preparation devices in which adsorptive membranes are easily sealed.

It is yet another object of the present invention to provide an adsorptive membrane that can be retrofitted into a conventional centrifugal sample preparation device.

SUMMARY OF THE INVENTION

The problems of the prior art have been overcome by the present invention, which provides an adsorptive sample preparation device and method effective for concentrating, desalting and/or purifying analytes in short periods of time. To that end, an adsorptive membrane is used to bind analytes, which analytes can then be eluted with a suitable desorption agent.

The adsorptive centrifugal filtration system of the present invention comprises:

(a) an adsorptive sample preparation device comprising:
  (1) a sample reservoir;
  (2) a base situated below the sample reservoir;
  (3) adsorptive filter means separating the sample reservoir from the base, said adsorptive filter means comprising an adsorptive membrane;
  (4) a support for said adsorptive filter means;
  (5) one or more filtrate ducts to allow for passage of filtrate from the filter means into the base;
  (6) means for providing a liquid tight seal between the periphery of the sample reservoir, the membrane, and the membrane support;
  (7) means for attaching the filter means to the base;
  (8) means for attaching the sample reservoir to the filter means; and (b) a fixed angle or swinging bucket centrifuge rotor to receive the adsorptive sample preparation device.

In a preferred form, the adsorptive filter means is a particle-laden semipermeable membrane having at least one of its major surfaces, preferably both of its major surfaces, covered with a thin fabric, and capable of binding analytes of less than about 10,000 molecular weight, generally less than 5000 molecular weight, which are typically difficult and slow to desalt on a 1000 and/or 3000 molecular weight cut-off ultrafiltration membrane.

In the method of the invention for concentrating biomolecules or desalting or purify from a solution, the sample reservoir of the above-described adsorptive sample preparation device is filled with an analyte solution, placed in a fixed angle or swinging bucket centrifuge rotor, the solution is driven through the membrane, the membrane is washed, and analyte obtained as a result of adsorption on the membrane is recovered by eluting with a suitable desorption agent.

BRIEF DESCRIPTION OF THE DRAWINGS

FIG. 1 is an exploded view of one embodiment of the centrifugal adsorptive sample preparation device of the present invention;

FIG. 4 is an exploded view of an alternative embodiment of the centrifugal adsorptive sample preparation device of the present invention;

FIG. 5 is a cross-sectional view of a portion of the device of FIG. 4;

FIG. 6 is a graph showing adsorption capacity of various membranes;

FIG. 7 is a graph showing adsorption capacity of several adsorptive device embodiments;

FIG. 8a is a chromatogram of a control peptide sample in accordance with Example 2;

FIG. 13 is an exploded view of an alternative embodiment of the centrifugal adsorptive sample preparation device of the present invention; and FIG. 14 is a cross-sectional view of the device of FIG. 13.

DETAILED DESCRIPTION OF THE INVENTION

Figure 10A:
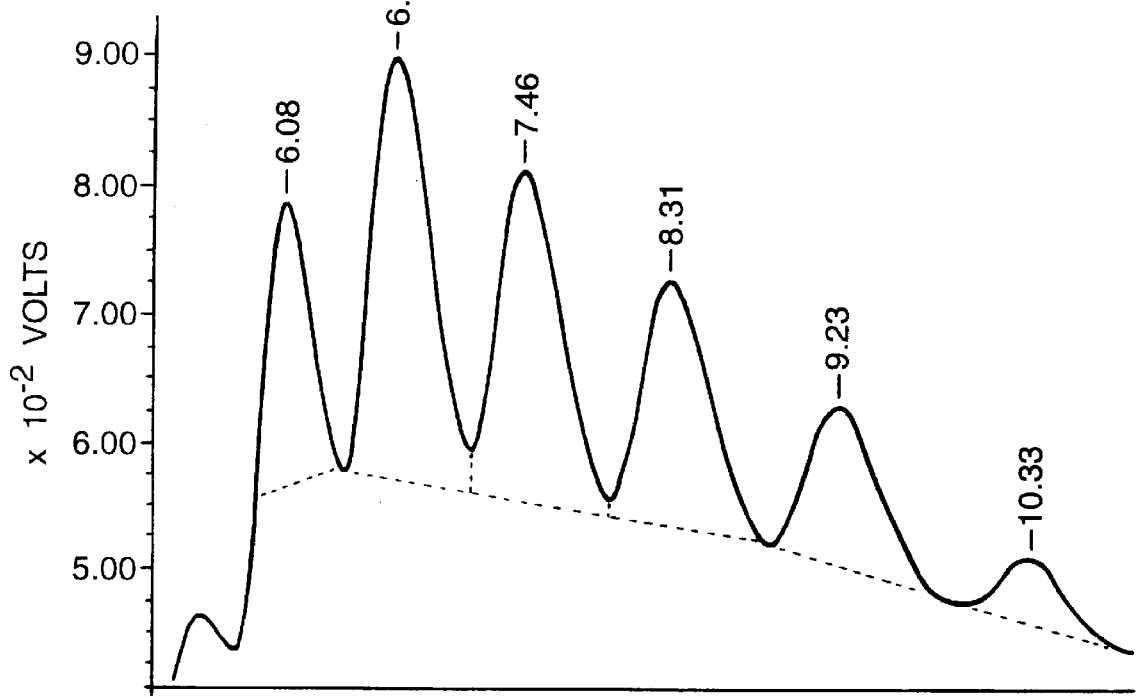
FIG. 10a is a chromatogram of a control oligonucleotide sample in accordance with Example 4.
Figure 10B:
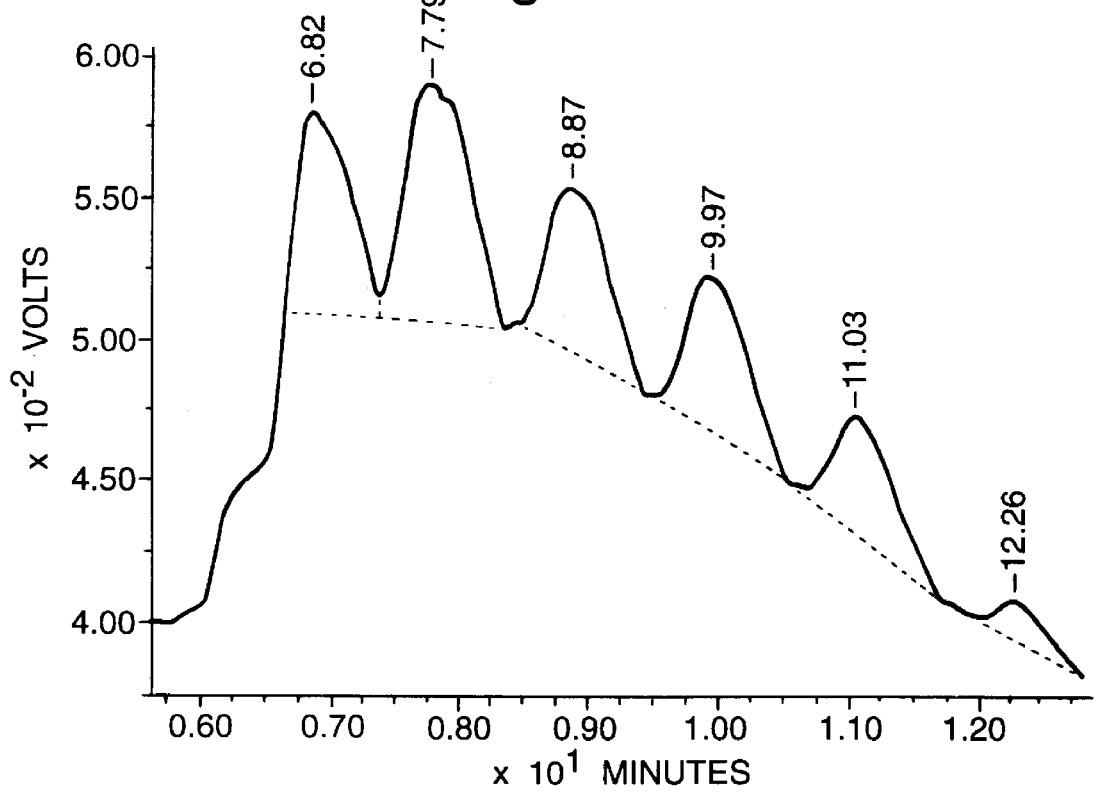
FIG. 10b is a chromatogram of a desorbed oligonucleotide sample in accordance with Example 4.
Figure 11:
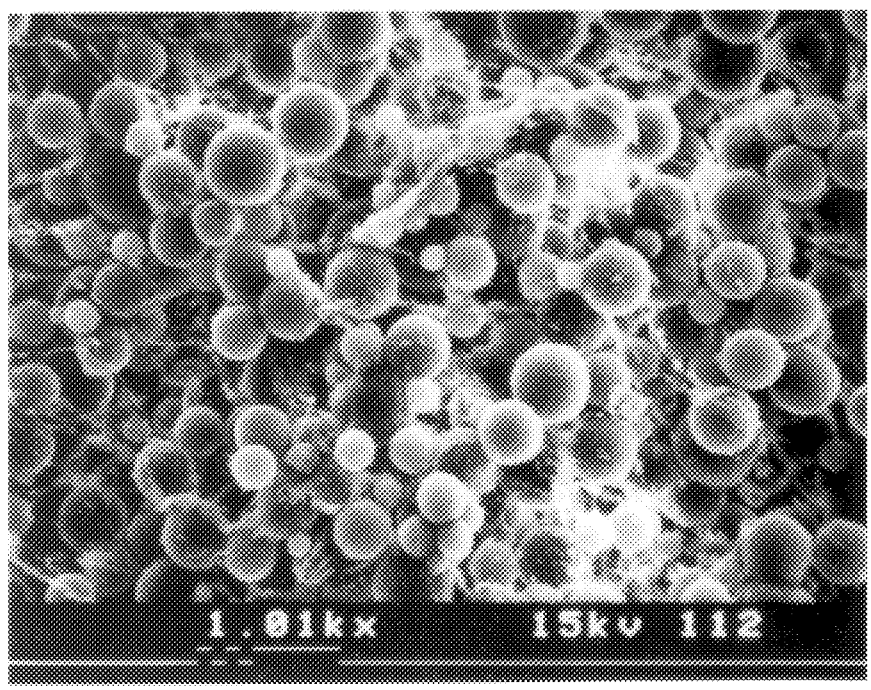
FIG. 11 is a scanning electron microscope view of an adsorptive membrane suitable for the present invention.
Figure 12:
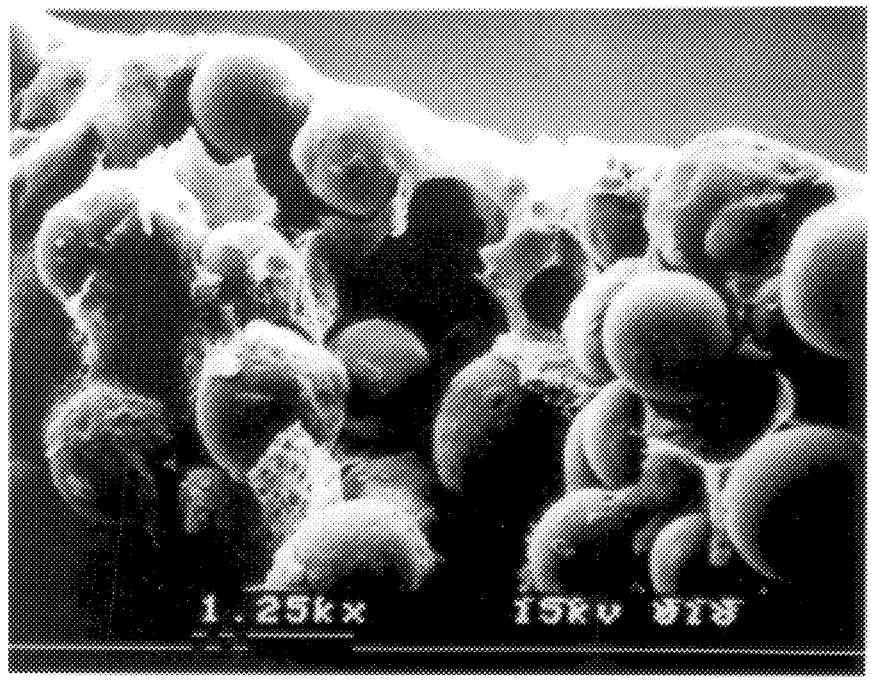
FIG. 12 is a scanning electron microscope view of another adsorptive membrane suitable for use in the present invention.

Those skilled in the art will recognize that many different adsorptive membranes can be used in the present invention, depending upon the desired objectives. The ideal membrane has rapid adsorption kinetics, does not require a chaotropic agent, has a capacity and selectivity appropriate for the application, and allows for elution of bound analyte with an evaporatable/lyophylizable desorption agent. Suitable adsorptive membranes are polymer bound particle laden adsorptive membranes, such as those comprised of chromatographic beads (which may be functionalized) which have been adhered together with a binder, such as polytetrafluoroethylene (PTFE) fibrils, as shown in FIGS. 10 and 11. Specifically, FIG. 10 illustrates a polymer bound particle laden adsorptive membrane manufactured and sold by Minnesota Mining and Manufacturing under the name EMPORE, and disclosed in U.S. Pat. No. 5,147,539, the disclosure of which is hereby incorporated by reference. This is a strong cation exchange membrane or disk designed to adsorb positively charged polypeptides and therefore ideal for removing non-proteinaceous anionic or neutral contaminants from peptide samples. It contains 80 Angstrom (pore diameter), 8 micron (particle diameter) spherical polystyrenedivinylbenzene (PSDVB) beads functionalized with a sulfonic acid ($-SO_3^-$), and is 0.020+/−0.002 inches thick, has a flow rate of 15–30 ml/min-cm$^2$ with water at 10 psi (room temperature), and is 90% (+/−2) particles by weight and 10% (+/−2) PTFE by weight. The particles are insoluble, non-swellable sorptive particles enmeshed in a PTFE fibril matrix. This membrane offers a mixed cationic/hydrophobic surface character which adsorbs many types of biomolecules, yet passes most salts, organics and non-cationic detergents. Moreover, bound analytes can be efficiently desorbed with acids, bases and/or salts in the presence of organic.

Another suitable polymer bound particle laden adsorptive membrane is illustrated in FIG. 11. This membrane is comprised of about 60% spherical silica functionalized with a sulfonic acid, 20% PVDF binder and 20% support, and is manufactured by Amicon, Inc. In a preferred form, the silica and binder are cast onto both sides of a support. The support can be the same spunbonded or polyolefin-based fabrics mentioned below. Other functional membranes can include spherical polystyrenedivinylbenzene beads adhered together in a PVDF matrix and including a support, or can comprise other micron-size spherical resin particles that may be derivatized with other functional groups, including PSDVB or silica-based anion exchangers (quaternary amines, for example, PSDVB($-N(CH_3)_3^+$); reverse phase media, e.g., silica-based $C_2$, $C_4$, $C_6$, $C_8$, or $C_{18}$; as well as PSDVB mixed ion exchangers (cation and anion), to accommodate a variety of applications for peptides, oligonucleotides and other biomolecules ("biomolecules" as used herein includes amino acids, peptides (molecular weight generally less than about 5000), small proteins (molecular weight generally greater than about 5000 and less than about 10,000) and oligonucleotides. Those skilled in the art will recognize that other matrices with alternative selectivities (e.g., anion-exchange) can also be used, especially for classes of molecules other than peptides. Devices in accordance with the present invention may incorporate a plurality of functional membranes having resin materials with different functional groups to fractionate analytes that vary by charge and hydrophobicity; alternately, a plurality of devices containing different individual functional membranes may be used in combination to achieve a similar result.

In accordance with the present invention, the polymer bound, particle laden adsorptive membrane must be sealed in the sample preparation device to prevent leakage of sample therefrom. However, in view of the small size of many of these devices, and therefore of the membrane contained therein, and in view of the clay-like texture of some of these adsorptive membranes, handling of the membrane and sealing of the membrane in the device is extremely problematic; the membrane is often deformed, cut or torn during handling or during the sealing operation, resulting in device failure. Accordingly, the preferred embodiment of the present invention is characterized by providing a thin, porous fabric layer over at least the membrane surface facing the sample reservoir, preferably over both that surface and the surface facing the base, prior to sealing the membrane in the device (these surfaces are usually the "major surfaces" of the membrane, and will be referred to as such hereinafter). The porous fabric serves multiple functions, including (1) maintaining membrane shape and improving handleability, especially during membrane cutting and placement in the sample preparation device; (2) preventing membrane cuts at the seal junction in the sample preparation device; (3) acting as a shim in the sample preparation device; and (4) aiding in flow control by holding the membrane flat and functioning as a flow restrictor. Flow restriction increases the liquid contact time with the membrane media and can be beneficial in some applications.

The present inventors surprisingly found that the adsorptive membrane having one or even both of its major surfaces covered with fabric can be effectively sealed in various types of conventional centrifugal sample preparation devices without requiring any modification of the device.

The fabrics used must not deleteriously impede flow, and should be inert to the components of the sample being purified or concentrated. Suitable thin fabrics are those composed of spunbonded polyester, although polyolefin-based fabrics such as polypropylene/polyethylene also can be used. The thickness of the fabric is preferably between about 0.0005 to about 0.005 inches, depending upon the nature of the sample preparation device. If the fabric is too thin, it will not be strong enough to maintain membrane dimensionality. If the membrane is too thick, it can impede assembly of the sample preparation device, such as where a "snap fit" sealing arrangement is used as per the embodiment illustrated in FIGS. 1 and 2. A preferred thin fabric for use in the snap-fit device shown in FIG. 1 is HOLYTEX fabric, commercially available from Ahlstrom Filtration, Inc., composed of polyester having a thickness of 0.0015+/−0.0003 inches; a weight of 0.4–0.5 oz/yd$^3$; an air permeability of 450–675 cfm/ft$^2$; a tensile strength of 2–6 lbs/inch, MD and 1.5–3.5 lbs/inch, CD; and an elongation of 17–33%, MD and 31–58%, CD. Thicker fabrics can be used with devices that are sealed using an O-ring, such as the device shown in FIG. 4. Another suitable fabric is VILE-DON® FO2432, composed of a non-woven polypropylene/polyethylene, weighing 30 g/m$^2$, having a tensile strength in the machine direction of >50 N/5 cm and in the cross direction of >70 N/5 cm, and having an air permeability at 0.5 mBar of 700 dm$^3$/s.m$^2$.

The fabric can be applied to the membrane by any suitable means. The present inventors have found that the fabric tends to adhere to the membrane on its own; no adhesive is necessary. The preferred method of applying the fabric to the membrane is with a die, suitable shaped according to the shape of the membrane, which is usually circular. Wax paper is placed on a polypropylene cutting surface. The fabric, which is generally commercially available as rollstock, is placed on the wax paper, followed by a sheet (available in 1'×1' sheets) of the membrane. An additional sheet of fabric can then be placed over the membrane where it is desirable to cover both major membrane surfaces. The die is then forced down and simultaneously sandwiches and cuts the components into a suitable shape.

Turning now to FIG. 1, there is shown generally at 1 a sample preparation device in accordance with one embodiment of the present invention. The device 1, which is generally suitable for ultrafiltration of sample volumes of about 0.5 ml, comprises a sample reservoir 2, a base 3 and a vial 4 having a vial cap 5. A polymer bound, particle laden adsorptive membrane 6 is disposed between the reservoir 2 and the base 3, and is covered with a thin polyester-based fabric 7 and 7a on each major surface.

Figure 2:
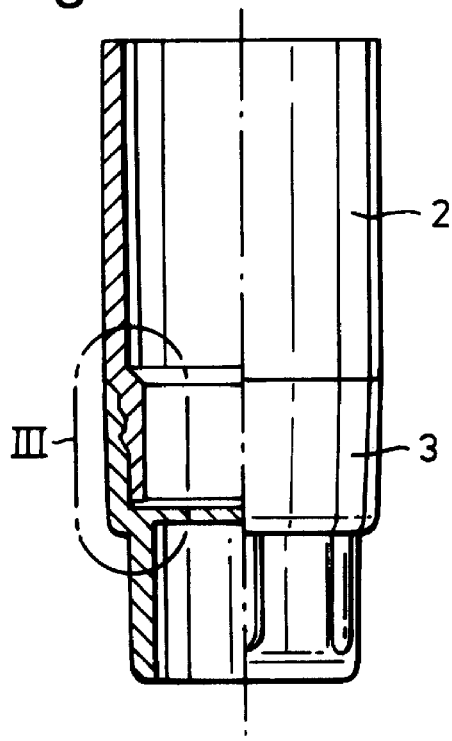
FIG. 2 is a cross-sectional view of a portion of the device of FIG. 1.
Figure 3:
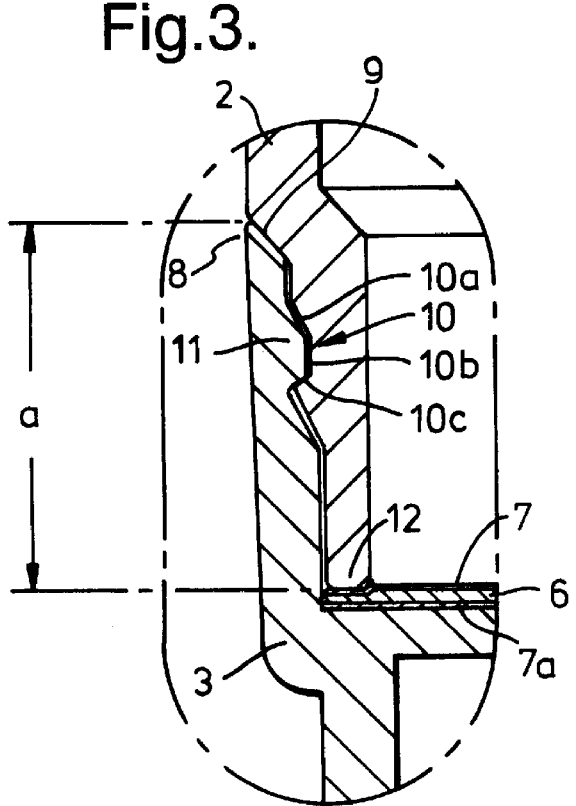
FIG. 3 is a detailed view of a portion of the device of FIG. 2.

FIGS. 2 and 3 illustrate the snap-fit locking mechanism of the device that provides the liquid seal. To that end, reservoir 2 has a first annular groove 9 having about a 45° angle that receives a corresponding angled annular top surface 8 of base 3. A second annular groove 10 of reservoir 2 includes a first annular angled portion 10a, and a second annular vertical portion 10b, and terminates in annular angled seat 10c. This second annular groove 10 receives a corresponding annular projection 11 of base 3. Once the reservoir 2 is snapped into the base 3 (or vice versa), the seat 10c in reservoir 2 locks the base 3 in place by preventing the annular projection 11 of base 3 from downward vertical movement. The length "a" of the portion of reservoir 2 is chosen so that when the reservoir 2 is assembled and locked into the base 3, the annular base 12 of the reservoir 3 seals against the thin fabric of the adsorptive membrane as shown. One or more passageways or ducts are formed below the membrane 6 as a result of grooves in the base to allow for passage into base 3 (and ultimately vial 5) of sample not adsorbed onto the membrane 6.

The device shown in FIGS. 1–3 exhibits high extraction efficiency with short spin times. Capacity for peptides ranges from about 150 to about 400 μgs/device, depending on sample and rotor type used for centrifugation; fixed-angle rotors offer less capacity than horizontal rotors. For maximum adsorption, the sample's estimated total ionic strength should not exceed 0.1M in a 500 μl volume. If ionic strength is unknown, a method of serial dilutions can be used to ascertain whether competing ions are impacting adsorption. Solutes must have a positively charged moiety such as a primary, secondary or tertiary amine for adsorption to occur. Generally, the sample pH should be adjusted to a value below the pKa or pI of the analyte. Ammonium hydroxide or alcoholic HCl (1M), for example, can be used to elute the sample. Those skilled in the art understand that the particular eluting agent used depends on the identity of the analyte and can be readily determined.

FIGS. 4 and 5 illustrate a second embodiment of the present invention, generally applicable for ultrafiltration of sample volumes of about 2.0 ml. The device in FIG. 4 utilizes a cold formed crimp sealing mechanism wherein an O-ring is placed over the membrane which has been laid in the base. The reservoir is then inserted into the base and the excess lip of the base is molded over the reservoir lip to hold it in place. Thus, the reservoir 2' includes an annular lip or collar 16 that snaps into and is locked by annular flange 17 of base 3'. The base of the annular collar 16 engages the O-ring 13 to effect the seal. Since the O-ring 13 is somewhat compressible, the thickness of the fabric 7a (and optionally 7b) covering the adsorptive membrane 6 is not as critical; thicker fabrics can be used without impeding the ability of the device to seal.

FIGS. 13 and 14 illustrate a third embodiment of the present invention, generally used for ultrafiltration of sample volumes of about 250 μl. In this device, the base and the reservoir are an integral, single formed unit (thus, the vial 4" is performing the function that the base performed in the embodiments of FIGS. 1–3 and 4–5, in that it receives fluid passing through the membrane 6), and a press fit is used to seal the membrane in the device. Specifically, a base/reservoir unit 100 includes a plurality of ducts or passageways 15' formed in the bottom surface of base 103, below the membrane 6, to allow sample to be dispensed from said base/reservoir 100 into a vial 4". The membrane 6 and fabric layer 7 (and/or fabric layer 7a) are sandwiched in place at the base 103 with a hollow cylindrical press fit tube 200 (the base 103 of the base/reservoir 100 therefore also serves as a membrane support). The outer diameter of the tube 200 is slightly larger that the inner diameter of the base/reservoir 100, so that when tube 200 is press fit into the base/reservoir 100, a water-tight seal is formed. The tube 200 is forced down so as to contact the membrane 6 (or fabric layer 7 on the membrane 6) as shown in FIG. 14. Wall friction holds the tube 200 in place in the base/reservoir 100. Once the tube 200 is in place, the inside volume of the tube 200 serves as the sample reservoir. The base/reservoir 100 includes an annular flange 101 that is of a greater outside diameter than the diameter of the top of the vial 4", so that when the base/reservoir 100 is placed in the vial 4" for centrifugation, the annular flange 101 prevents the base/reservoir 100 from falling into the vial 4" and allows it to remain accessible. A cap 5' is preferably coupled to the vial 4" and is appropriately configured to fit into the bore 102 in the top of the base/reservoir 100.

Those skilled in the art will recognize that the principles of the present invention are not limited to any particle volume centrifugal device. Suitable devices include those ranging from 0.2 to 15 ml devices.

By minimizing membrane surface area for the required volumes, optimal adsorption/desorption of analytes in the sample can be achieved. Studies have shown that these devices achieve the required rate of passing sample that is slow enough for quantitative capture of analytes and fast enough to allow solvent passage in order to perform the required analysis. Results demonstrate that solvent must flow through the membrane as fast as 35 ml/min. Following passage of analyte and solvent through the membrane by centrifugation, the species of interest is adsorbed onto the membrane and subsequently removed by preferably first washing the membrane to eliminate unbound, unwanted impurities such as detergents, salts, etc., and then using a small volume of a less polar solvent capable of displacing and dissolving the sorbed species through the functional extraction membrane. If removal of loosely bound impurities is desired, a dilute desorbing agent (such as a desorbing agent having about 1/10th the concentration for complete desorption) can be used for the wash. If the elution volume was less than the original sample volume, a net concentration will have been achieved.

When compared to conventional, i.e., packed bed, extraction devices, the inventive device exhibits improved performance as a result of the small sized resin exchanger enmeshed in the binder (e.g., PTFE) fibril matrix, that allows for high extraction efficiency and fast flow rates without channeling to maintain a uniform flow while maximizing contact sites for analytes.

EXAMPLE 1

A variety of thin fabrics of varying thickness were applied to EmPore™-SCX adsorptive membranes and sealed in the sample preparation devices of FIG. 1. The ability of the devices to selectively adsorb was then evaluated using known amounts of cytochrome c. (Although cytochrome c is a protein with a molecular weight (12,000) larger than is preferable for such devices, it was utilized as a "worst case scenario", since such larger molecules diffuse slower. Furthermore, it has a visible absorbance at 410 nm, providing means for convenient quantitation.) The protein was introduced into a given unit to determine device capacity. This amount was determined by a colorimetric assay that measured the quantity of unbound or free (F) cytochrome c that passed into the filtrate. Optimal performance was determined by challenging devices with increasing amounts of cytochrome c in order to determine the maximum polypeptide adsorption capacity. Results comparing devices prepared with uncovered membrane ("No Htex"), membrane having only the major surface facing the sample reservoir covered with HOLLYTEX polyester fabric ("1 Htex"), and membrane having both major surfaces covered with HOLLYTEX fabric ("2 Htex"), are shown in FIG. 6. These data demonstrate that more cytochrome c is bound (B) to devices wherein one and both major surfaces of the membrane were covered with fabric. In addition, in the samples wherein the surface of the membrane facing the sample reservoir was covered with fabric, the fabric served to prevent the membrane from either cutting during assembly or buckling during high speed centrifugation. In the sample wherein both major surfaces of the membrane were covered, the fabric covering the surface of the membrane facing the base served to enhance binding efficiency.

FIG. 7 clearly shows that devices prepared with fabric on both major surfaces of the membrane were able to bind over 250 μgs of cytochrome c, compared to less than 170 μgs when only one major surface was covered with fabric.

EXAMPLE 2

Figure 8B:
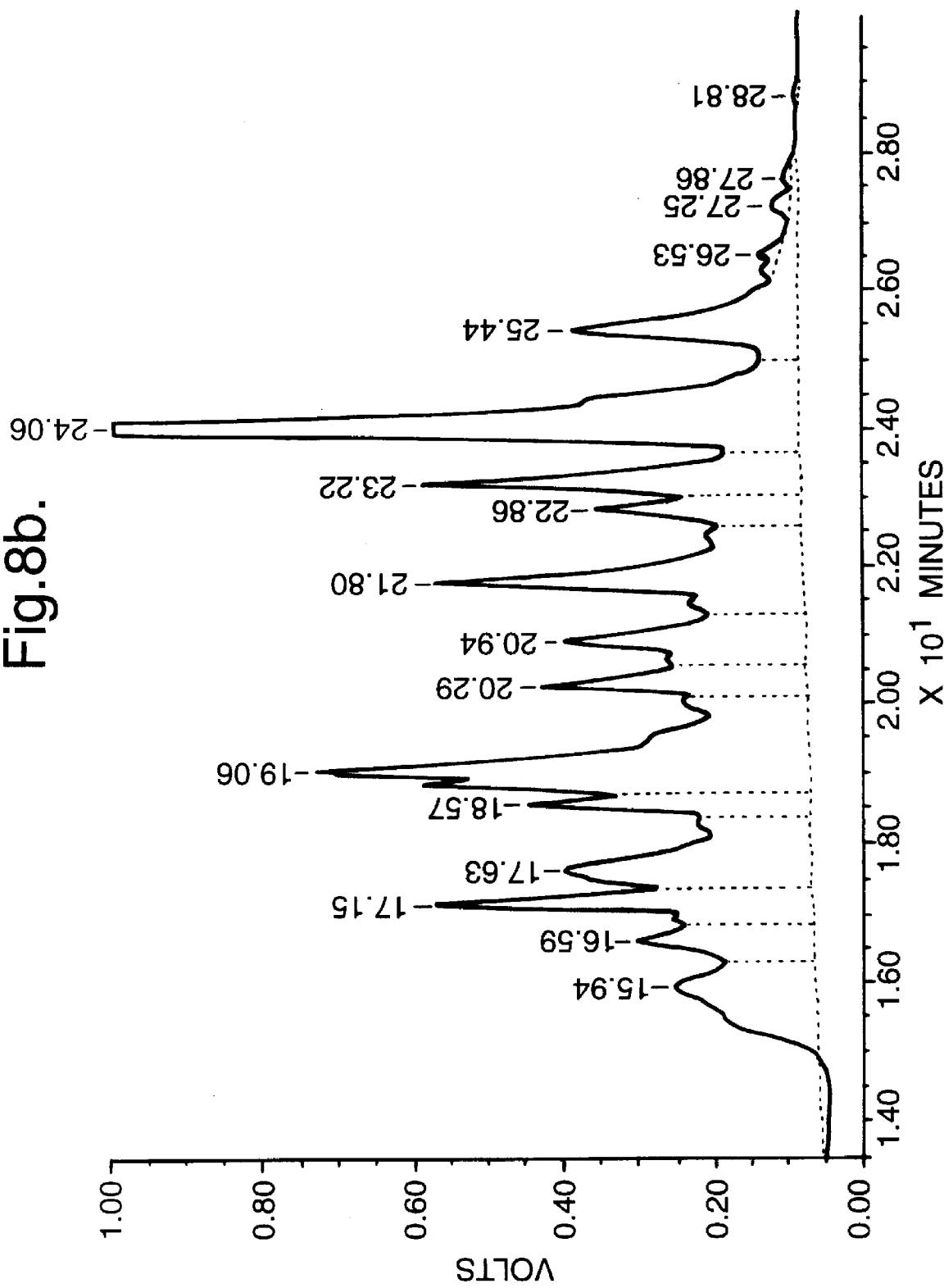
FIG. 8b is a chromatogram of a desorbed peptide sample in accordance with Example 2.

Cytochrome c was digested with trypsin to release multiple peptides which vary in charge and size. Approximately 150 μgs (in 400 μl) of digest were applied to the device of FIG. 1, centrifuged and desorbed for subsequent quantitation by reverse phase HPLC. The integration values of eluted peaks were then compared to the equivalent amount of sample applied directly to the HPLC column (control). To insure optimal binding, the pH was adjusted to 3. Following sample addition, the device was centrifuged for 15 seconds. 400 μl of dH$_2$O was the centrifuged through as a wash step to remove salts, detergents and other non-adsorbed solutes. Bound components were desorbed with two 50 μl aliquots of an alcoholic high pH eluant. The elution operation required only about one minute to perform. The released peptides were subsequently neutralized with acid, injected onto the column and chromatographed using an acetonitrile gradient. Results comparing peptides obtained from this procedure relative to the control are shown in FIGS. 8a and 8b. The chromatograms in FIGS. 8 and 8b are virtually identical, thus demonstrating efficient binding and elution. Peak integration results showed recoveries to range from 75% to 95%.

EXAMPLE 3

Figure 9A:
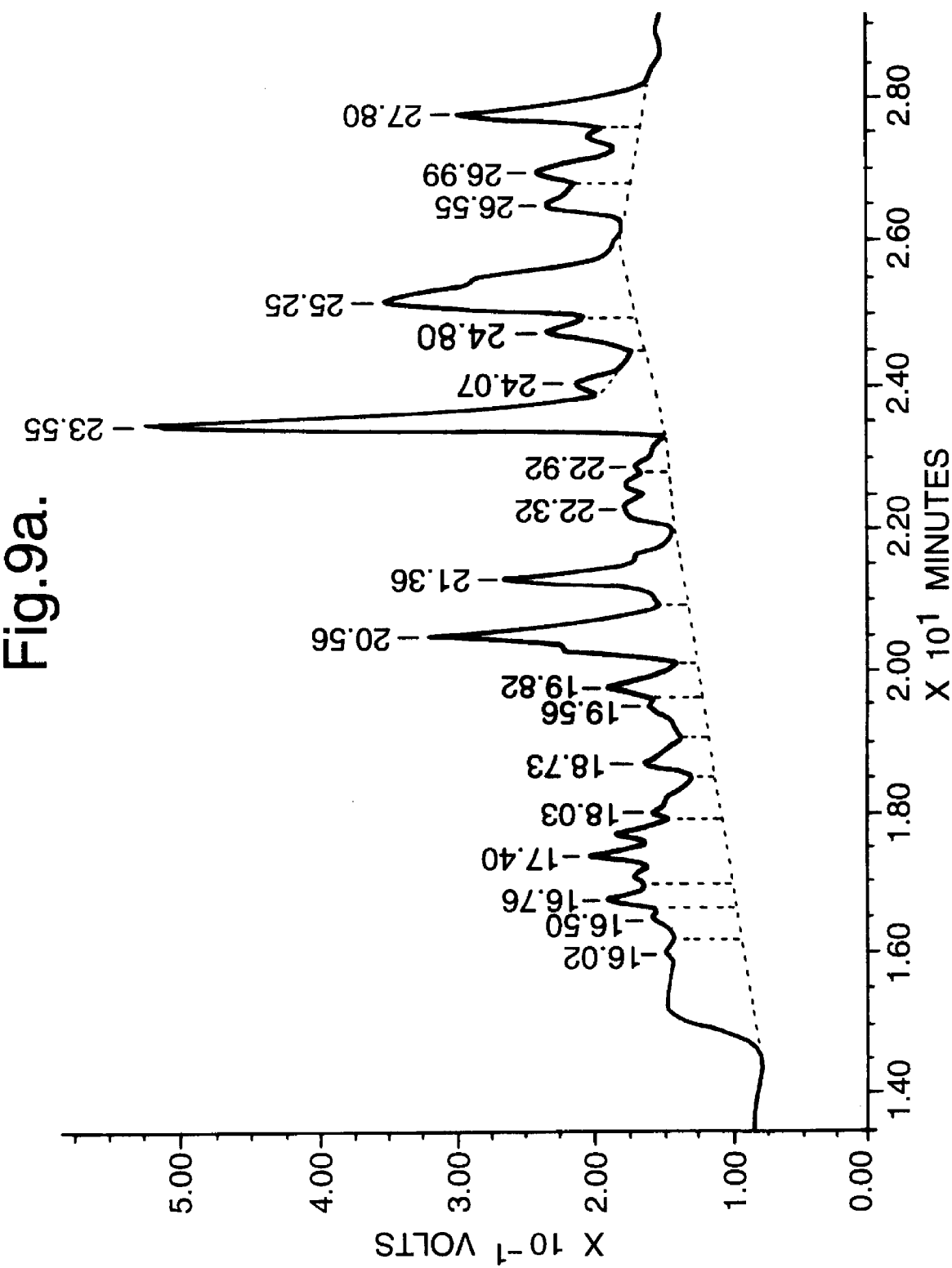
FIG. 9a is a chromatogram of a control peptide sample in accordance with Example 3.
Figure 9B:
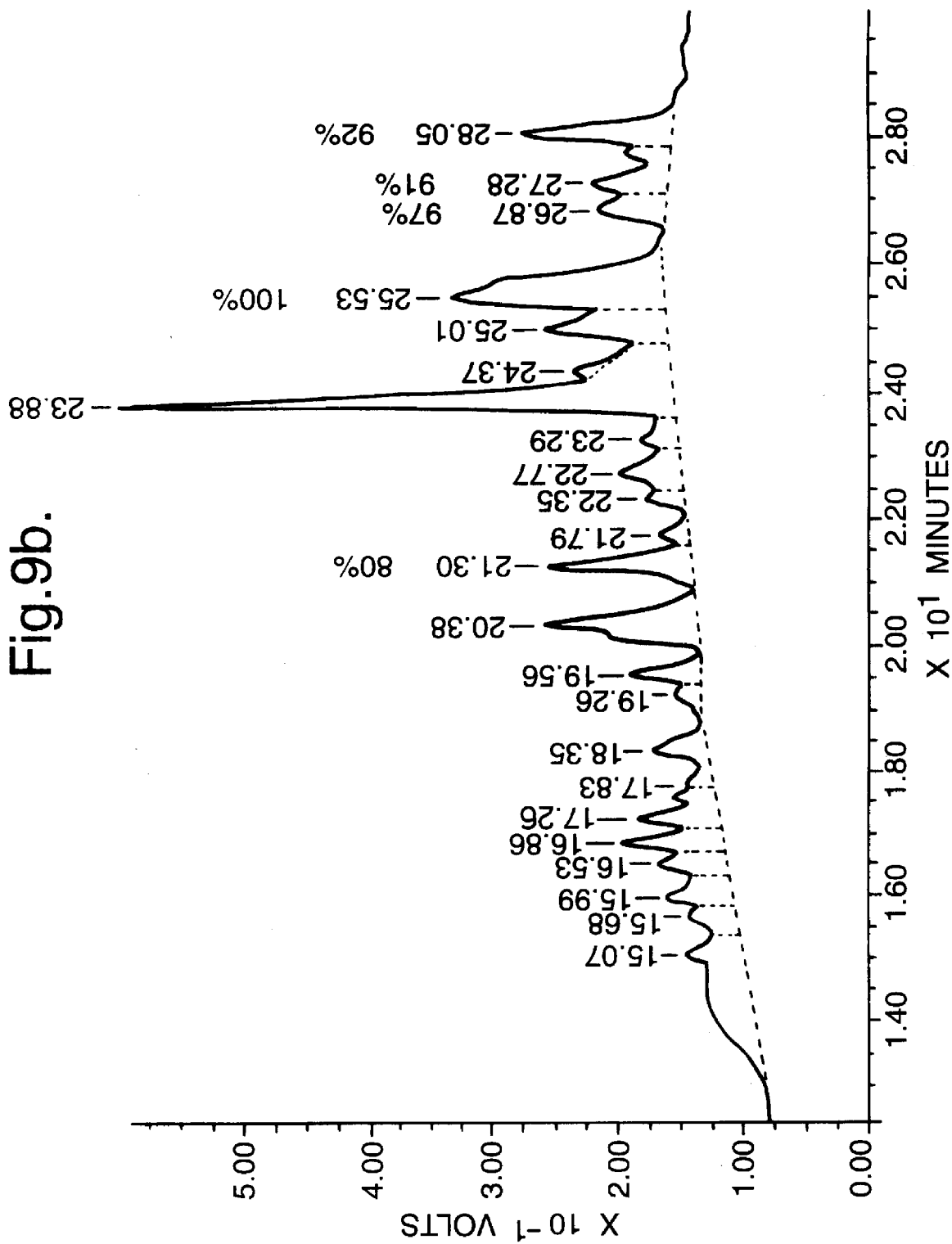
FIG. 9b is a chromatogram of a desorbed peptide sample in accordance with Example 3.

The procedure of Example 2 was repeated using Endo-lys c (enzyme) digestion of α-lactoglobulin which generates a completely different set of peptides than those of Example 2. The peptides were again bound, washed, eluted and analyzed. FIGS. 9a and 9b show the chromatograms, which again are virtually identical, thereby demonstrating the effectiveness of the device to selectively adsorb and desorb.

EXAMPLE 4

Approximately 20 picomoles of PCR primer polythymidillic acid consisting of 6 oligomers ranging in oligomer size of 19 to 24 are prepared for the device of FIG. 1 by diluting sample in a buffer (100 mM ammonium acetate pH 7.0). Following the addition of 10 μL of glacial acetic acid to 400 μL of sample (pH 3.5), the printers are centrifuged onto the device, washed with 400 μL of deionized water to remove unbound solutes, and finally eluted by adding 50 μL of 1N ammonium hydroxide in 50% methanol using 30 s high speed centrifugation. Samples were rapidly neutralized with HCl and applied onto a C18 reverse phase column in 100 mM triethylamine acetate and chromatographed with a shallow gradient of acetonitrile (0.5%/min). Comparison of the sample chromatogram to that of the eluate shows a high degree of recovery. These data clearly demonstrate that the device binds and elutes oligonucleotides. Therefore, such molecules can be concentrated and purified according to the present invention.

What is claimed is:

1. A centrifugal adsorptive sample preparation device, comprising:

first means for receiving a sample;

second means for dispensing said sample; and a polymer bound, particle laden adsorptive semipermeable membrane effective for selectively adsorbing biomolecules sealed between said first and said second means, said adsorptive semipermeable membrane having a first surface facing said first means and a second surface facing said second means, said adsorptive semipermeable membrane having a polyester or polyolefin fabric of a thickness of from about 0.0005 to about 0.005 inches on at least one of said first and second surfaces.

2. The centrifugal adsorptive sample preparation device of claim 1, wherein said adsorptive membrane comprises polystyrenedivinylbenzene beads.

3. The centrifugal adsorptive sample preparation device of claim 2, wherein said polystyrenedivinylbenzene beads are functionalized with a sulfonic acid.

4. The centrifugal adsorptive sample preparation device of claim 1, wherein said adsorptive membrane comprises silica, PVDF binder and a support.

5. The centrifugal adsorptive sample preparation device of claim 1, wherein said adsorptive membrane adsorbs biomolecular cations.

6. A centrifugal adsorptive sample preparation device, comprising:

first means for receiving a sample;

second means for dispensing said sample; and a polymer bound, particle laden adsorptive semipermeable membrane effective for selectively adsorbing biomolecules sealed between said first and said second means, said adsorptive semipermeable membrane having a first surface facing said first means and a second surface facing said second means, wherein both said first and second surfaces of said semipermeable membrane have a layer of polyester or polyolefin fabric thereon.

7. The centrifugal adsorptive sample preparation device of claim 6, wherein said adsorptive membrane comprises polystyrenedivinylbenzene beads.

8. The centrifugal adsorptive sample preparation device of claim 7, wherein said polystyrenedivinylbenzene beads are functionalized with a sulfonic acid.

9. The centrifugal adsorptive sample preparation device of claim 6, wherein said adsorptive membrane comprises silica, PVDF binder and a support.

10. A method of sealing an adsorptive membrane in a sample preparation device having a first means for receiving a sample and second means for dispensing said sample, and wherein one of said first and second means comprises a membrane support, comprising:

providing a layer comprising a polyester or polyolefin fabric having a thickness of from about 0.0005 to about 0.005 inches on a major surface of said adsorptive membrane;

placing said adsorptive membrane on said membrane support;

coupling said first and second means together with said membrane lodged in between.

11. The method of claim 10, wherein said adsorptive membrane comprises polystyrenedivinylbenzene beads.

12. The method of claim 10, wherein said adsorptive membrane comprises silica, PVDF binder and a support.

13. The method of claim 10, further comprising providing a layer comprising a polyester or polyolefin fabric on a second major surface of said adsorptive membrane.

14. The method of claim 10, wherein said first means comprises a sample reservoir.

15. A polymer bound, particle laden adsorptive membrane effective for selectively adsorbing analyte, said membrane comprising a first surface adapted to be exposed to said analyte, said first surface having a layer of polyester- or polyolefin-based fabric thereon.

16. The polymer bound, particle laden adsorptive membrane of claim 15, wherein said membrane further comprises a second surface opposite said first surface; said second surface having a layer of polyester- or polyolefin-based fabric thereon.

17. The polymer bound, particle laden adsorptive membrane of claim 16, further comprising polystyrenedivinylbenzene beads.

18. The polymer bound, particle laden adsorptive membrane of claim 16, further comprising silica, PVDF binder and a support.

19. The polymer bound, particle laden adsorptive membrane of claim 15, further comprising polystyrenedivinylbenzene beads.

20. The polymer bound, particle laden adsorptive membrane of claim 15, further comprising silica, PVDF binder and a support.

21. An adsorptive centrifugal filtration device comprising:

a sample reservoir;

a base situated below said sample reservoir;

adsorptive filter means separating said sample reservoir from said base, said adsorptive filter means comprising a semipermeable polymer bound, particle laden adsorptive membrane having a first surface facing said sample reservoir and a second surface opposite said first surface, and having a polyester or polyolefin-based fabric of a thickness of from about 0.0005 to about 0.005 on at least one of said first and second surfaces;

a support for said adsorptive filter means;

one or more filtrate ducts in said base to allow for passage of filtrate from said filter means into said base; and means for providing a liquid tight seal between the periphery of said sample reservoir, said membrane, and said membrane support.

22. The filtration device of claim 21, wherein said polyester or polyolefin-based fabric is on said first surface.

23. The filtration device of claim 22, wherein said said second surface has a layer of polyester or polyolefin based fabric thereon.

24. A method of selectively adsorbing biomolecules having a molecular weight less than about 10,000 from a sample, comprising:

contacting said sample with a semipermeable polymer bound, particle laden adsorptive membrane having a polyester of polyolefin-based fabric of a thickness of from about 0.0005 to about 0.005 on at least one surface thereof so as to cause said biomolecules to be adsorbed by said membrane;

subjecting said membrane to centrifugation so as to cause sample not adsorbed by said membrane to pass through said membrane.

25. The method of claim 24, further comprising desorbing said biomolecules from said membrane with an agent effective for eluting said biomolecules.

26. The method of claim 25, wherein the volume of said sample is greater than the volume of said eluting agent, thereby resulting in a concentration of said biomolecules.

27. The method of claim 24, wherein said sample not adsorbed comprises impurities, thereby resulting in a purification of said biomolecules upon elution.

* * * * *